US009340561B2

(12) United States Patent
Umezaki et al.

(10) Patent No.: US 9,340,561 B2
(45) Date of Patent: May 17, 2016

(54) ORGANIC SILICON COMPOUND AND SILANE COUPLING AGENT CONTAINING THE SAME

(75) Inventors: Makiko Umezaki, Toyama (JP); Daisuke Sakuma, Funabashi (JP); Taito Nishino, Shiraoka (JP); Takahiro Kishioka, Toyama (JP); Yoshiomi Hiroi, Toyama (JP); Shigeo Kimura, Toyama (JP); Tomoya Ohashi, Toyama (JP); Yuki Usui, Toyama (JP)

(73) Assignee: NISSAN CHEMICAL INDUSTRIES, LTD., Tokyo (JP)

( * ) Notice: Subject to any disclaimer, the term of this patent is extended or adjusted under 35 U.S.C. 154(b) by 187 days.

(21) Appl. No.: 14/345,002

(22) PCT Filed: Aug. 28, 2012

(86) PCT No.: PCT/JP2012/071697
§ 371 (c)(1),
(2), (4) Date: Mar. 14, 2014

(87) PCT Pub. No.: WO2013/038901
PCT Pub. Date: Mar. 21, 2013

(65) Prior Publication Data
US 2014/0370182 A1 Dec. 18, 2014

(30) Foreign Application Priority Data
Sep. 16, 2011 (JP) ................................. 2011-203681

(51) Int. Cl.
| | |
|---|---|
| *C07F 7/08* | (2006.01) |
| *A61L 27/28* | (2006.01) |
| *A61L 27/54* | (2006.01) |
| *A61L 29/08* | (2006.01) |
| *A61L 29/16* | (2006.01) |
| *A61L 31/08* | (2006.01) |
| *A61L 31/16* | (2006.01) |
| *C09D 5/16* | (2006.01) |
| *C07F 7/18* | (2006.01) |

(52) U.S. Cl.
CPC ............... *C07F 7/0818* (2013.01); *A61L 27/28* (2013.01); *A61L 27/54* (2013.01); *A61L 29/08* (2013.01); *A61L 29/16* (2013.01); *A61L 31/08* (2013.01); *A61L 31/16* (2013.01); *C07F 7/1836* (2013.01); *C09D 5/1625* (2013.01); *A61L 2300/424* (2013.01)

(58) Field of Classification Search
None
See application file for complete search history.

(56) References Cited

U.S. PATENT DOCUMENTS 5,639,555 A 6/1997 Bishop

FOREIGN PATENT DOCUMENTS

| | | |
|---|---|---|
| JP | A-54-63025 | 5/1979 |
| JP | A-7-228702 | 8/1995 |
| JP | A-9-295989 | 11/1997 |
| JP | A-2000-279512 | 10/2000 |
| JP | A-2007-130194 | 5/2007 |
| JP | A-2008-274151 | 11/2008 |
| JP | A-2009-91330 | 4/2009 |

(Continued)

OTHER PUBLICATIONS

English language Abstracts of JP 2012-148436, Aug. 9, 2012.*

(Continued)

*Primary Examiner* — Erma Cameron
(74) *Attorney, Agent, or Firm* — Oliff PLC

(57) ABSTRACT

There is provided a novel organic silicon compound that can be used for a silane coupling agent. An organic silicon compound of Formula (1):

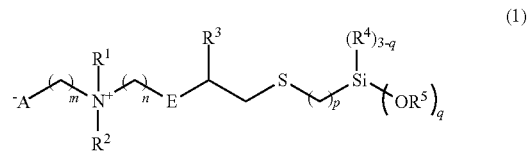

(where $A^-$ is Formula (2) or Formula (3):

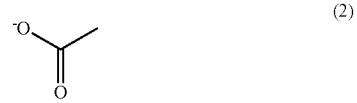

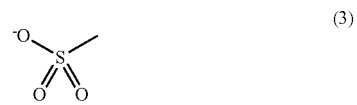

E is Formula (4) or Formula (5):

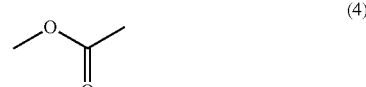

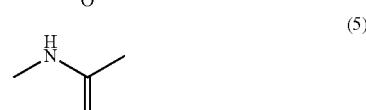

$R^1$ and $R^2$ are each independently a $C_{1-5}$ alkyl group, $R^3$ is a hydrogen atom or a methyl group, $R^4$ and $R^5$ are each independently a $C_{1-5}$ alkyl group, m, n, and p are each independently an integer of 1 to 5, and q is an integer of 1 to 3).

11 Claims, No Drawings

(56) References Cited

FOREIGN PATENT DOCUMENTS

| | | | |
|---|---|---|---|
| JP | A-2010-57745 | | 3/2010 |
| JP | A-2011-136985 | | 7/2011 |
| JP | 2011-219637 | * | 11/2011 |
| JP | 2012-148436 | * | 8/2012 |

OTHER PUBLICATIONS

English language Abstracts of JP 2011-219637, Nov. 4, 2011.*

Qiu et al., "A Novel Zwitterionic Silane Coupling Agent for Nonthrombogenic Biomaterials," *Chinese Journal of Polymer Science*, 2005, vol. 23, No. 6, pp. 611-617.

Estephan et al., "Zwitteration as an Alternative to PEGylation," *Langmuir*, 2011, vol. 27, pp. 6794-6800.

International Search Report issued in International Patent Application No. PCT/JP2012/071697 dated Oct. 30, 2012.

Written Opinion issued in International Patent Application No. PCT/JP2012/071697 dated Oct. 30, 2012.

* cited by examiner

ORGANIC SILICON COMPOUND AND SILANE COUPLING AGENT CONTAINING THE SAME

This application is a National Stage of PCT/JP2012/071697, which claims priority of JP 2011-203681, filed Sep. 16, 2011. The entire disclosures of the prior applications are hereby incorporated by reference in their entirety.

TECHNICAL FIELD

The present invention relates to a betaine or sulfobetaine type organic silicon compound that has both positive and negative stable charges in one molecule thereof and that can suppress adherence of biological substances such as protein and cells such as platelets by performing surface treatment on inorganic substances such as silicon and glass or resins such as polyethylene.

BACKGROUND ART

Coming into contact with an external material such as an artificial material, a biological system recognizes the artificial material as a foreign body. This causes various types of foreign-body reactions such as thrombus formation, immunization reaction, and inflammatory reaction with the passage of time. For this reason, pharmaceutical drugs, for example, anticoagulant agents such as heparin, and immunosuppressive agents need to be used in combination with the use of medical appliances such as artificial organs.

However, the use of the anticoagulant agents or other agents may cause various side reactions such as hepatic dysfunction and allergic reaction.

To solve these issues, a material for medical application is disclosed that employs poly(2-methacryloyloxyethyl phosphorylcholine) (called an MPC polymer in the present specification, hereinafter) including at the side chain of a polymer chain, phosphorylcholine that is an amphoteric phospholipid similar to the biological membrane (see Patent Document 1 and Patent Document 2, for example).

A material for medical application is disclosed that employs a high molecular weight polymer of N-methacryloyloxyethyl-N,N-dimethylammonium-α-N-methylcarboxybetaine (called a CMB polymer in the present specification, hereinafter) (see Patent Document 3, Patent Document 4, and Patent Document 5, for example).

Coating the surface of a material with the MPC polymer or the CMB polymer enables blood coagulation to be suppressed even without the use of an anticoagulant agent.

PRIOR ART DOCUMENTS

Patent Documents

Patent Document 1: Japanese Patent Application Publication No. S54-063025 (JP S54-063025 A)

Patent Document 2: Japanese Patent Application Publication No. 2000-279512 (JP 2000-279512 A)

Patent Document 3: Japanese Patent Application Publication No. 2007-130194 (JP 2007-130194 A)

Patent Document 4: Japanese Patent Application Publication No. 2008-274151 (JP 2008-274151 A)

Patent Document 5: Japanese Patent Application Publication No. 2010-057745 (JP 2010-057745 A)

SUMMARY OF THE INVENTION

Problem to be Solved by the Invention

However, it takes time and labor to perform the processes of synthesizing the MPC polymer and the CMB polymer and further preparing solutions containing the polymers. It is an object of the present invention to provide a non-polymer substance with which the surface of a substrate can be directly coated by preparing a solution thereof and that has an effect equivalent to the conventional MPC polymer and CMB polymer.

Means for Solving the Problem

To solve the above-described disadvantages, the inventors of the present invention have found a betaine type or a sulfobetaine type organic silicon compound that has both positive and negative stable charges in one molecule thereof and that prevents adherence of biological substances such as protein and cells such as platelets. Specifically, one aspect of the present invention provides an organic silicon compound of Formula (1):

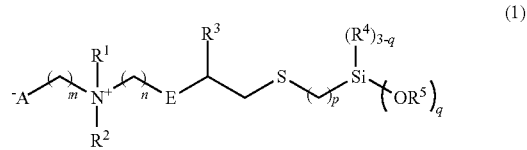

(where $A^-$ is Formula (2) or Formula (3):

E is Formula (4) or Formula (5):

a carbonyl group in each of Formula (4) and Formula (5) is bonded to a carbon atom to which $R^3$ is bonded, $R^1$ and $R^2$ are each independently a $C_{1-5}$ alkyl group, $R^3$ is a hydrogen atom or a methyl group, $R^4$ and $R^5$ are each independently a $C_{1-5}$ alkyl group, m, n, and p are each independently an integer of 1 to 5, and q is an integer of 1 to 3).

Another aspect of the present invention provides a silane coupling agent (surface treatment agent) comprising: the organic silicon compound; a polar organic solvent; and water.

Still another aspect of the present invention provides an adherence inhibitor for a biological substance or a cell, comprising the silane coupling agent.

Still another aspect of the present invention provides a method for immobilizing a silane coupling agent, comprising the step of applying the silane coupling agent to a substrate or immersing a substrate in the silane coupling agent.

Effects of the Invention

Surface treatment can be performed on an inorganic substance such as silicon and glass or a resin such as polyethylene (called a substrate in the present specification, hereinafter) using the silane coupling agent (surface treatment agent) containing the organic silicon compound of the present invention. The surface is coated with a betaine or a sulfobetaine that has both positive and negative stable charges in one molecule thereof. This can prevent biological substances such as protein and cells such as platelets from adhering to the surface of the inorganic substance or the resin without the use of polymers such as the MPC polymer and the CMB polymer.

MODES FOR CARRYING OUT THE INVENTION

The organic silicon compound of Formula (1) can be synthesized by, for example, allowing a betaine to react with a mercaptosilane.

Preferable examples of the betaine as a raw material of the organic silicon compound of Formula (1) include
N-methacryloyloxyethyl-N,N-dimethylammonium-α-N-methylcarboxybetaine,
N-methacryloyloxyethyl-N,N-dimethylammonium-α-N-propylsulfoxybetaine, and
N-methacryloylaminopropyl-N,N-dimethylammonium-α-N-propylsulfoxybetaine.

Preferable examples of the mercaptosilane as the other raw material of the organic silicon compound of Formula (1) include 3-mercaptopropyltrimethoxysilane, 3-mercaptopropyltriethoxysilane, 3-mercaptopropylmethyldimethoxysilane, (mercaptomethyl)dimethoxysilane, (mercaptomethyl)dimethylethoxysilane, and mercaptomethyltrimethoxysilane.

When the organic silicon compound is used for the surface treatment of an inorganic material serving as a substrate, the inorganic material is not particularly limited. Examples thereof include silicon, copper, iron, aluminum, zinc, or alloys of these, glass, silica, aluminium oxide, aluminium hydroxide, and magnesium oxide.

When the organic silicon compound is used for the surface treatment of a resin serving as a substrate, the resin is not particularly limited. Examples thereof include polyethylene, polypropylene, polystyrene, poly(vinyl chloride), nylon, polyurethane, polyurea, poly(lactic acid), poly(glycolic acid), poly(vinyl alcohol), poly(vinyl acetate), poly(meth)acrylic acid, a poly(meth)acrylic acid derivative, polyacrylonitrile, poly(meth)acrylamide, a poly(meth)acrylamide derivative, polysulfone, polycarbonate, cellulose, and a cellulose derivative.

The organic silicon compound can be used for surface treatment of pharmaceutical preparations, quasi drugs, medical appliances and the like. Examples of the medical appliances include drug delivery system materials, subsidiary materials for forming, packaging materials, blood vessel prostheses, hemodialysis membranes, catheters, guide wire, contact lenses, blood filters, blood preservation packs, endoscopes, artificial organs, biochips, cell culture sheets, and carbohydrate chain synthesis equipment, but the medical appliances are not particularly limited thereto.

The biological substance in the present specification is a basic material constituting a living body. Examples thereof include protein, nucleic acid, various saccharides, amino acids, nucleoside, lipid, and vitamins. Adherence of some of these biological substances is suppressed by the use of the silane coupling agent (surface treatment agent) containing the organic silicon compound of the present invention. Examples of such biological substances include protein, nucleic acid, various saccharides, amino acids, nucleoside, lipid, and vitamins, preferably, protein, nucleic acid, various saccharides, and further preferably, protein.

The cell in the present specification is the most basic unit constituting a living body and includes, as its elements, cytoplasm and various types of cell organelles inside the cell membrane. In the present specification, the cell may or may not include a nucleus containing DNA. Examples of animal-derived cells according to the present invention include reproductive cells such as spermatozoa and ova, somatic cells constituting a living body, stem cells, precursor cells, cancer cells separated from a living body, cells (cell strains) that are separated from a living body, have acquired immortalization potential, and are maintained stably outside the body, cells that are separated from a living body and genetically modified artificially, and cells that are separated from a living body and whose nuclei are exchanged artificially. Examples of the somatic cells constituting a living body include fibroblasts, bone marrow cells, B-lymphocytes, T-lymphocytes, neutrophils, erythrocytes, platelets, macrophages, monocytes, osteocytes, bone marrow cells, pericytes, dendritic cells, keratinocytes, adipocytes, mesenchymal cells, epithelial cells, epidermal cells, endothelial cells, vascular endothelial cells, liver parenchymal cells, chondrocytes, cumulus cells, neural cells, glial cells, neurons, oligodendrocytes, microglia, astrocytes, cardiac cells, esophageal cells, muscle cells (smooth muscle myocytes and skeletal myocytes, for example), pancreatic beta cells, melanocytes, hematopoietic progenitor cells, and mononuclear cells, but these are not limiting examples. Examples of the somatic cells include cells collected from any tissues such as the skin, the kidney, the spleen, the adrenal gland, the liver, the lung, the ovary, the pancreas, the uterus, the stomach, the colon, the small intestine, the large intestine, the bladder, the prostate gland, the testis, the thymus, the muscle, the connective tissue, the bone, the cartilage, the vascular tissue, the blood, the heart, the eye, the brain, and the nerve tissue. The stem cells are cells that have both the ability to duplicate the cell itself and the ability to differentiate into other cells in a plurality of lines. Examples thereof include embryonic stem cells (ES cells), embryonal carcinoma cells, embryonic germ stem cells, induced pluripotent stem cells (iPS cells), neural stem cells, hematopoietic stem cells, mesenchymal stem cells, hepatic stem cells, pancreatic stem cells, muscle stem cells, reproductive stem cells, intestinal stem cells, cancer stem cells, and hair follicle stem cells, but these are not limiting examples. The precursor cells are cells in the middle stage of differentiation from the stem cells into specific somatic cells or reproductive cells. The cancer cells are cells that are derived from somatic cells and have acquired infinite proliferative capacity. The cell strains are cells that have acquired infinite proliferative capacity by in vitro artificial operation. Examples thereof include HCT116, Huh7, HEK293 (human embryonal renal cell), HeLa (human cervical cancer cell strain), HepG2 (human liver cancer cell strain), UT7/TPO (human leukemia cell strain), CHO (Chinese hamster ovary cell strain), MDCK, MDBK, BHK, C-33A, HT-29, AE-1, 3D9, Ns0/1, Jurkat, NIH3T3, PC 12, S2, Sf9, Sf21, High Five, and Vero, but these are not limiting examples.

Adherence of some of these cells is suppressed by the use of the silane coupling agent (surface treatment agent) containing the organic silicon compound of the present invention. Examples of such cells include reproductive cells such as spermatozoa and ova, somatic cells constituting a living body, stem cells, precursor cells, cancer cells separated from a living body, cells (cell strains) that are separated from a living body, have acquired immortalization potential, and are maintained stably outside the body, cells that are separated from a living body and genetically modified artificially, and cells that are separated from a living body and whose nuclei are exchanged artificially; preferably, somatic cells constituting a living body, stem cells, precursor cells, cancer cells separated from a living body, and cells (cell strains) that are separated from a living body, have acquired immortalization potential, and are maintained stably outside the body; more preferably, somatic cells constituting a living body, cancer cells separated from a living body, and cells (cell strains) that are separated from a living body, have acquired immortalization potential, and are maintained stably outside the body; even more preferably, somatic cells constituting a living body; and most preferably, platelets.

The silane coupling agent (surface treatment agent) containing the organic silicon compound of the present invention can efficiently suppress adherence of biological substances and cells and thus can be used as a reagent for research on biological substances and cells. For example, to clarify a factor that adjusts differentiation and proliferation of cells or tissues, cells cultured under the coexistence of cells and the target factor, the number or the type of biological substances obtained from the cells, cell surface differentiation markers, and the change in expressed genes are analyzed. In this analysis, the use of the silane coupling agent of the present invention suppresses adherence of biological substances and cells, enabling target biological substances and cells to be efficiently recovered. In the analysis of the target factor, the skilled person appropriately selects culture conditions, culture equipment, the type of culture media, the type of silane coupling agents and their contents, the type of additives and additive contents, culture periods, culture temperatures, and the like. The cells proliferated or emerging by cultivation can be observed with a microscope standard in the technical field of the present invention. In this observation, the cultured cells may be stained with a specific antibody. The expressed genes changed due to the target factor can be detected through extraction of deoxyribonucleic acid (DNA) or ribonucleic acid (RNA) from the cultured cells, by Southern blotting, Northern blotting, RT-PCR, or other methods. The cell surface differentiation markers allow detection by ELISA or flow cytometry using a specific antibody and observation of the effect of the target factor on differentiation and proliferation.

The silane coupling agent (surface treatment agent) containing the organic silicon compound of the present invention is prepared by, for example, adding water and a polar organic solvent such as methanol, ethanol, and propylene glycol monomethyl ether to the organic silicon compound to dilute the mixture to 0.001% by mass to 20% by mass. An organic acid may further be added thereto in order to adjust the pH of the silane coupling agent. Examples of the organic acid include acetic acid, formic acid, and a lactic acid.

The method of performing surface treatment on the substrate with the silane coupling agent of the present invention is not particularly limited. The substrate can be treated by, for example, immersion, coating (spin coating, spray coating, etc.), or vacuum evaporation.

More precisely, the silane coupling agent of the present invention is immobilized by the process of applying the silane coupling agent onto a substrate and baking the silane coupling agent, then the process of washing the substrate with a polar solvent, and the process of drying the substrate. Alternatively, the silane coupling agent is immobilized by the process of immersing a substrate in the silane coupling agent, then the process of washing the substrate with a polar solvent, and the process of drying the substrate. Examples of the polar solvent used in the washing process include water or polar organic solvents contained in the silane coupling agent.

EXAMPLES

Specific examples according to the present invention are described below, but do not limit the present invention. The $CO_2$ concentration (%) in a $CO_2$ incubator is indicated by % by volume of $CO_2$ in the atmosphere. PBS means phosphate buffered saline (manufactured by Sigma-Aldrich Co. LLC.). FBS means fetal bovine serum (manufactured by Biological industries Ltd.).

Synthesis Example 1

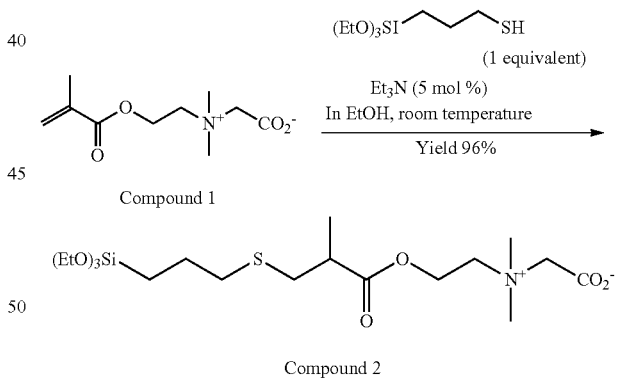

Into a 500 ml four neck flask equipped with a magnetic stirrer, 20.03 g of Compound 1, 22.15 g of (3-mercaptopropyl) triethoxysilane, 0.48 g of triethylamine, and 80 g of ethanol were added, and the mixture was stirred for 24 hours at room temperature. The reaction solution was concentrated and dried to produce 40.56 g of Compound 2 (yield: 96%).

$^1$H-NMR (400 MHz) in $CDCl_3$: 0.69-0.74 ppm (m, 2H), 1.23 ppm (t, J=7.0 Hz, 9H), 1.22-1.28 ppm (m, 3H), 1.62-1.73 ppm (m, 2H), 2.51-2.56 ppm (m, 2H), 2.57-2.68 ppm (m, 1H), 2.69-2.80 ppm (m, 2H), 3.37 ppm (s, 6H), 3.81 ppm (q, J=7.0 Hz, 6H), 3.96 ppm (s, 2H), 4.06-4.21 ppm (m, 2H), 4.47-4.63 ppm (m, 2H)

Synthesis Example 2

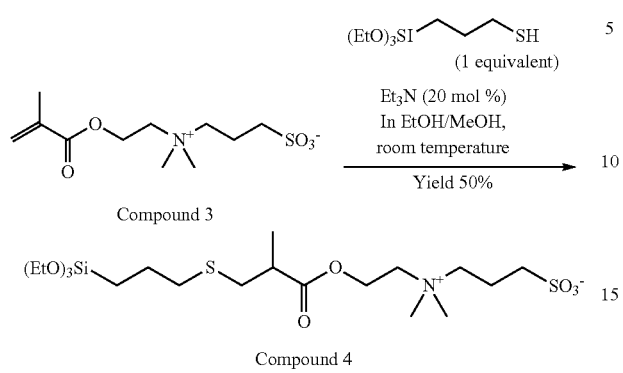

Into a 300 ml four neck flask equipped with a magnetic stirrer, 15.00 g of Compound 3, 12.81 g of (3-mercaptopropyl) triethoxysilane, 1.09 g of triethylamine, 60 g of ethanol, and 20 g of methanol were added, and the mixture was stirred for 2 hours at room temperature. The reaction solution was concentrated, and 60 g of hexane was then added thereto. The precipitated crystal was filtrated and dried to produce 13.81 g of Compound 4 (yield: 50%).

$^1$H-NMR (400 MHz) in CDCl$_3$: 0.68-0.76 ppm (m, 2H), 1.23 ppm (t, J=7.0 Hz, 9H), 1.22-1.28 ppm (m, 3H), 1.62-1.72 ppm (m, 2H), 2.21-2.34 ppm (m, 2H), 2.53 ppm (dd, J=7.0 Hz, 8.2 Hz, 2H), 2.55-2.65 ppm (m, 1H), 2.68-2.80 ppm (m, 2H), 2.85-2.94 ppm (m, 2H), 3.29 ppm (s, 6H), 3.74-3.87 ppm (m, 4H), 3.81 ppm (q, J=7.0 Hz, 6H), 4.56-4.62 ppm (m, 2H)

(Preparation 1 of Silane Coupling Agent)

Acetic acid was added to a solvent with a concentration of propylene glycol monomethyl ether (PGME)/water=9/1% by volume to prepare a solvent with a pH of 4.0. Subsequently, each of the organic silicon compounds produced in Synthesis Example 1 and Synthesis Example 2 was dissolved in the solvent so that the resultant mixture had a concentration of 1% by mass, thereby preparing a silane coupling agent.

Example 1

A glass substrate (TEMPAX Float [registered trademark], 50×50 mm, a thickness of 1 mm) was immersed in 10 ml of the silane coupling agent containing Compound 2 produced in Synthesis Example 1 and was left still at 40° C. for 24 hours. The resultant glass substrate was taken out from the silane coupling agent, then was washed with PGME, and air dried.

Example 2

A glass substrate of the same kind as the glass substrate used in Example 1 was immersed in 10 ml of the silane coupling agent containing Compound 4 produced in Synthesis Example 2 and was left still at 40° C. for 24 hours. The resultant glass substrate was taken out from the silane coupling agent, then was washed with PGME, and air dried.

Example 3

0.5 ml of the silane coupling agent containing Compound 2 produced in Synthesis Example 1 was applied onto a glass substrate of the same kind as the glass substrate used in Example 1 by a spin coater. The resultant substrate was baked on a hot plate at 100° C. for 15 minutes. Subsequently, the substrate was washed with PGME and air dried.

Example 4

0.5 ml of the silane coupling agent containing Compound 4 produced in Synthesis Example 2 was applied onto a glass substrate of the same kind as the glass substrate used in Example 1 by a spin coater. The resultant substrate was baked on a hot plate at 100° C. for 15 minutes. Subsequently, the substrate was washed with PGME and air dried.

Comparative Example 1

A glass substrate of the same kind as the glass substrate used in Example 1 was washed with PGME and air dried.

(Contact Angle Measurement)

The contact angle relative to each surface of the glass substrates treated in Example 1 to Example 4 and Comparative Example 1 was measured using water and diiodomethane. The contact angle was measured by a drop method using a contact angle meter (manufactured by Kyowa Interface Science Co., Ltd.) and was calculated by a θ/2 method. Table 1 below shows the results.

(Adsorption Experiment of Fluorescent Protein)

Fluorescent labeled bovine serum albumin (FITC-BSA, manufactured by Sigma-Aldrich Co. LLC.) was dissolved in phosphate saline (PBS, pH 7.4) to prepare 100 μg/ml of an FITC-BSA solution. 0.5 ml of the FITC-BSA solution was added onto each surface of the glass substrates treated in Example 1 to Example 4 and Comparative Example 1, and the resultant substrate was left still at 37° C. for 30 minutes. Subsequently, the FITC-BSA solution was removed from each surface of the glass substrates, and the resultant substrate was washed with PBS used as the solvent and air dried.

Excitation was performed at a wavelength of 490 nm for 10 seconds and fluorescence was measured at a wavelength of 520 nm by a fluorescence microscope (manufactured by Olympus Corporation). Adsorption of FITC-BSA was examined from the fluorescence intensity. Table 1 below shows the results.

TABLE 1

| | Contact angle (water) | Contact angle (diiodomethane) | Fluorescence intensity |
|---|---|---|---|
| Example 1 | 34.6° | 30.7° | 0.0 |
| Example 2 | 28.9° | 30.6° | 0.0 |
| Example 3 | 18.2° | 27.8° | 7.2 |
| Example 4 | 15.0° | 30.0° | 22.4 |
| Comparative Example 1 (Treated with fluorescent protein) | — | — | 60.4 |
| Comparative Example 1 (Not treated with fluorescent protein) | 58.0° | 53.1° | 0.0 |

The contact angle measurement results show decrease in the contact angle relative to water and diiodomethane, of each of the glass substrates treated in Example 1 to Example 4, as compared with the glass substrate (not treated with fluorescent protein) treated in Comparative Example 1. It is considered from this decrease that the glass substrates were coated with the respective silane coupling agent containing Compound 2 and the silane coupling agent containing Compound 4.

As a result of the adsorption experiment of fluorescent protein, the fluorescence intensity of each of the glass substrates treated in Example 1 and Example 2 was lower than that of the glass substrate (treated with fluorescent protein) treated in Comparative Example 1 and was equal to that of the glass substrate (not treated with fluorescent protein) treated in Comparative Example 1. It is considered that this result is obtained because both positive and negative ionic moieties of Compound 2 and Compound 4 were arranged at the surface layers of the glass substrates to inhibit adsorption of fluorescent protein. The fluorescence intensity of each of the glass substrates treated in Example 3 and Example 4 was also lower than that of the glass substrate (treated with fluorescent protein) treated in Comparative Example 1, thereby suppressing adsorption of fluorescent protein.

(Preparation 2 of Silane Coupling Agent)

Each of the organic silicon compounds produced in Synthesis Example 1 and Synthesis Example 2 was dissolved in 99.5% by volume of ethanol (containing 0.5% by volume of water) so as to be a 10 mM solution, thereby preparing a silane coupling agent.

Example 5

A glass substrate (TEMPAX Float [registered trademark], φ12 mm, a thickness of 1 mm) whose surface was washed by $O_2$ etching was immersed in 100 ml of the 10 mM ethanol solution containing Compound 2 produced in Synthesis Example 1 and was left still at room temperature for 48 hours. The resultant glass substrate was taken out from the solution, then was washed with ethanol, and air dried.

Example 6

A glass substrate of the same kind as the glass substrate used in Example 5 was immersed in 100 ml of the 10 mM ethanol solution containing Compound 4 produced in Synthesis Example 2 and was left still at room temperature for 48 hours. The resultant glass substrate was taken out from the solution, then was washed with ethanol, and air dried.

Comparative Example 2

A glass substrate of the same kind as the glass substrate used in Example 5 was stored in a plastic case for 1 week.

(Preparation of Platelet Solution)

0.5 ml of a 3.8% by mass sodium citrate solution was mixed with 4.5 ml of blood collected from a healthy volunteer. The resultant mixture were subjected to centrifugation [refrigerated centrifuge 5900 (manufactured by KUBOTA Manufacturing Corporation), 1000 rpm/10 minutes, room temperature], and platelet-rich plasma (PRP) at the upper phase was recovered. Subsequently, the lower phase was subjected to centrifugation (the above centrifuge, 3500 rpm/10 minutes, room temperature), and the platelet-poor plasma (PPP) at the upper phase was recovered. The number of platelets in the PRP was counted by an automatic multipurpose erythrocyte analyzer (XT-2000i, manufactured by SYSMEX CORPORATION), and then, a solution was prepared so as to have a PRP platelet concentration of $30 \times 10^4$ cells/μl using the PPP.

(Platelet Adherence Experiment)

Each of the glass substrates treated in Example 5, Example 6, and Comparative Example 2 was set to a 24-well flat-bottomed microplate (manufactured by Corning Incorporated), and 300 μl of the PRP solution prepared to the above platelet concentration was added thereto. The resultant plate was left still in a $CO_2$ incubator at 37° C. for 90 minutes while the carbon dioxide concentration was maintained at 5%. The PRP in the plate was removed, and then, the residue was washed with 3 ml of phosphate buffered saline (PBS) five times. Subsequently, 2 ml of a solution of 2.5% by volume of glutaraldehyde in PBS was added thereto, and the resultant mixture was left still at 4° C. for a day. The solution of glutaraldehyde in PBS was then removed therefrom, and the resultant mixture was washed with 3 ml of ultrapure water (Milli-Q water) five times. The resultant mixture was further washed with 1 ml of 70% ethanol water (v/v) three times and was air dried. This experiment was performed twice (Run-1 and Run-2).

(Electron Microscope Observation)

Pt—Pd was evaporated onto each of the glass substrates treated in Example 5, Example 6, and Comparative Example 2 and subjected to the platelet adherence experiment for 1 minute by an ion sputter (E-1030, manufactured by Hitachi High-Technologies Corporation). Subsequently, the adherence of platelets was observed with an electron microscope (S-4800, manufactured by Hitachi High-Technologies Corporation) at ×1000 magnification.

The number of adhering platelets was counted at five points on the glass substrate with the electron microscope. The counted values at each point were averaged to be designated as the number of adhering platelets in Run-1 or Run-2. The number of adhering platelets in Run-1 and Run-2 was then averaged, thereby comparing the platelet adherence to each of the glass substrates treated in Example 5, Example 6, and Comparative Example 2. Table 2 below shows the results.

TABLE 2

|  | Run-1 | Run-2 | Average value |
|---|---|---|---|
| Example 5 | 3.0 | 29.6 | 16.3 |
| Example 6 | 0.2 | 0.0 | 0.1 |
| Comparative Example 2 | Difficult to count due to a large amount of deposits | Difficult to count due to a large amount of deposits | Difficult to count due to a large amount of deposits |

As a result of the platelet adherence experiment, a large amount of deposits were observed on the glass substrate treated in Comparative Example 2, and thus, it was difficult to count the number of adhering platelets. In contrast, the number of adhering platelets on each of the glass substrates treated in Example 5 and Example 6 was countable, and the deposits thereon were apparently few as compared with the glass substrate treated in Comparative Example 2.

(Preparation of Cells)

Cells used were human embryonal renal cell strains Hek293 (manufactured by DS Pharma Biomedical Co., Ltd.), human liver cancer cell strain HepG2 (manufactured by DS Pharma Biomedical Co., Ltd.), human cervical cancer cell strain HeLa (manufactured by DS Pharma Biomedical Co., Ltd.), human embryonal lung cell strain MRC5 (manufactured by DS Pharma Biomedical Co., Ltd.), and Chinese hamster ovary cell strain CHO (manufactured by DS Pharma Biomedical Co., Ltd.). Culture media used in cultivation of these cells were EMEM culture media (manufactured by Wako Pure Chemical Industries, Ltd.) containing HeLa, Hek293, and MRC5: 10% (v/v) FBS, DMEM culture media (manufactured by Wako Pure Chemical Industries, Ltd.) containing HepG2: 10% (v/v) FBS, and DMEM/F-12 culture media (manufactured by Sigma-Aldrich Co. LLC.) containing CHO: 10% (v/v) FBS. The cells were left still using a petri dish with a diameter of 10 cm (10 ml of a culture medium) for two or more days in a state where the carbon dioxide concentration in a 37° C. $CO_2$ incubator was maintained at 5%. Subsequently, the cells were washed with 5 ml of PBS, and then, 1 ml of a trypsin-EDTA solution (manufactured by Invitrogen Corporation) was added thereto, thereby peeling off the cells. The resultant mixture was suspended with 10 ml of the above culture medium. The suspension was subjected to centrifugation (the centrifuge used in the preparation of the platelet solution, 1500 rpm/3 minutes, room temperature). The supernatant was then removed therefrom, and the above culture medium was added thereto, thereby preparing a cell suspension.

(Cell Adherence Experiment)

Each of the glass substrates treated in Example 5, Example 6, and Comparative Example 2 was set to a 24-well flat-bottomed microplate (manufactured by Corning Incorporated). 1 ml of the prepared cell suspension was added to each glass substrate so as to be $2.5 \times 10^5$ cells/well. Subsequently, the microplate was left still in a $CO_2$ incubator at 37° C. for 24 hours while the carbon dioxide concentration was maintained at 5%.

(Count of Number of Adhering Cells)

24 hours later, each of the glasses treated in Example 5, Example 6, and Comparative Example 2 subjected to the cell adherence experiment was transferred to another 24-well flat-bottomed microplate and was washed with 1 ml of PBS. The PBS was removed therefrom, and then, 500 µl of a trypsin-EDTA solution (manufactured by Invitrogen Corporation) was added thereto. 5 minutes to 10 minutes later, 500 µl of a DMEM culture medium (manufactured by Wako Pure Chemical Industries, Ltd.) containing 10% (v/v) FBS was added to the resultant mixture, and the peeled cells were transferred to a 1.5 ml micro test tube (manufactured by Eppendorf Co., Ltd.). After the centrifugation (manufacture by TOMY SEIKO CO., LTD., model number: MX-307, 1500 rpm/3 minutes, room temperature), the supernatant was removed therefrom. 100 µl of a DMEM culture medium (manufactured by Wako Pure Chemical Industries, Ltd.) containing 10% (v/v) FBS was added to the residue, thereby preparing a cell suspension. A trypan blue staining fluid was added to this suspension in equal proportions, and then, the number of living cells (adhering cell number) was counted using a hemocytometer (manufactured by ERMA INC.).

After 24 hour cultivation, the number of cells adhering to each of the glass substrates treated in Example 5, Example 6, and Comparative Example 2 was compared. Table 3 below shows the result. In Table 3, "–" indicates that the number of adhering cells was difficult to be counted.

TABLE 3

| | Cell number (×1000) | | |
|---|---|---|---|
| | Example 5 | Example 6 | Comparative Example 2 |
| Hek293 | 49 cells | 43 cells | 106 cells |
| HepG2 | 48 cells | 78 cells | 98 cells |
| HeLa | — | 13 cells | 23 cells |
| MRC5 | 69 cells | 99 cells | 155 cells |
| CHO | 198 cells | — | 337 cells |

As a result of the cell adherence examination, after the 24 hour cultivation, the number of cells adhering to each of the glass substrates treated in Example 5 and Example 6 was lower than that of the glass substrate treated in Comparative Example 2 in any of the cells.

The invention claimed is:

1. An organic silicon compound of Formula (1):

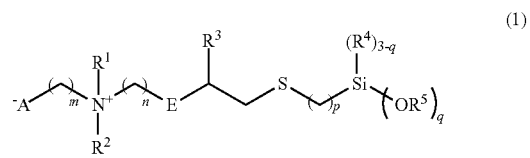

where $A^-$ is Formula (2) or Formula (3):

E is Formula (4) or Formula (5):

a carbonyl group in each of Formula (4) and Formula (5) is bonded to a carbon atom to which $R^3$ is bonded, $R^1$ and $R^2$ are each independently a $C_{1-5}$ alkyl group, $R^3$ is a hydrogen atom or a methyl group, $R^4$ and $R^5$ are each independently a $C_{1-5}$ alkyl group, m, n, and p are each independently an integer of 1 to 5, and q is an integer of 1 to 3.

2. A silane coupling agent comprising:
the organic silicon compound as claimed in claim 1;
a polar organic solvent; and
water.

3. The silane coupling agent according to claim 2, further comprising an organic acid.

4. An adherence inhibitor for a biological substance or a cell, comprising the silane coupling agent as claimed in claim 2.

5. The adherence inhibitor according to claim 4, wherein the cell is a platelet.

6. A method for immobilizing a silane coupling agent, the method comprising the steps of:
applying the silane coupling agent according to claim 2 onto a substrate and baking the silane coupling agent;
washing the substrate with a polar solvent; and
drying the substrate.

7. A method for immobilizing a silane coupling agent, the method comprising the steps of:
immersing a substrate in the silane coupling agent according to claim 2;
washing the substrate with a polar solvent; and
drying the substrate.

8. An adherence inhibitor for a biological substance or a cell, comprising the silane coupling agent as claimed in claim 3.

9. The adherence inhibitor according to claim 8, wherein the cell is a platelet.

10. A method for immobilizing a silane coupling agent, the method comprising the steps of:
- applying the silane coupling agent according to claim 3 onto a substrate and baking the silane coupling agent;
- washing the substrate with a polar solvent; and
- drying the substrate.

11. A method for immobilizing a silane coupling agent, the method comprising the steps of:
- immersing a substrate in the silane coupling agent according to claim 3;
- washing the substrate with a polar solvent; and
- drying the substrate.

\* \* \* \* \*